United States Patent [19]

Berbers et al.

[11] Patent Number: 5,646,252

[45] Date of Patent: Jul. 8, 1997

[54] HEMOGLOBIN COMPOSITION AND PREPARATION THEREOF

[75] Inventors: Wilhelmus Antonius Berbers, Utrecht; Petrus Theodorus Maria Biessels, Oegstgeest; Willem Karel Bleeker, Amsterdam; Joachim Cornelis Bakker, Koog aan de Zaan, all of Netherlands

[73] Assignee: Staat der Nederlanden, De Minister van Defensie, voor deze: Het Hoofd van de Afdeling Militair Geneeskundig Beleid, Netherlands

[21] Appl. No.: 543,478

[22] Filed: Oct. 16, 1995

Related U.S. Application Data

[63] Continuation-in-part of Ser. No. 281,260, Jul. 27, 1994, abandoned, which is a continuation of Ser. No. 777,353, Feb. 10, 1992, abandoned.

[51] Int. Cl.$^6$ .................................................. C07K 14/805
[52] U.S. Cl. ................................................................ 530/385
[58] Field of Search ................................... 500/385; 514/6

[56] References Cited

U.S. PATENT DOCUMENTS

| 4,826,811 | 5/1989 | Sehgal et al. | 514/6 |
| 4,857,636 | 8/1989 | Hsia | 530/385 |

OTHER PUBLICATIONS

Arnone, "Structure of Human Deoxyhemoglobin Specifically Modified with Pyridoxal Compounds", J. Biol., vol. 155, 1977, pp. 627–642.

Benesch, et al., "Affinity Labeling of the Polyphosphate Binding Site of Hemoglobin", Biochemistry, vol. 11, No. 19, 1972, pp. 3576–3582.

Benesch, et al., "Bis–Pyridoxal Polyphosphates: A New Class of Specific Intramolecular Crosslinking Agents for Hemoglobin", Biochemical and Biophysical Research Communications, vol. 156, No. 1, 1988, pp. 9–14.

Benesch, et al., "The Stability of the Heme–Globin Linkage in Some Normal, Mutant, and Chemically Modified Hemoglobins", Journal of Biological Chemistry, vol. 265, No. 25, 1990, pp. 14881–14885.

Berbers, et al., "Biophysical Characteristics of hemoglobin intramolecularly cross–linked and polymerized", J. Lab Clin Med, 1991, pp. 157–165.

Bleeker, et al., "Prolonged vascular retnetion of a hemoglobin solution modified by cross–linking with 2–nor–2–formylpyridoxal 5'–phosphate", J Lab Clin Med, 1986, pp. 448–455.

Den Boer, et al., "Scaling Up The Production Of Hemoglobin Solutions", Annual Report, CLB, Amsterdam, pp. 5–6.

DeVenuto, et al., "Preparation and Evaluation of Pyridoxalated–Polymerized Human Hemoglobin", Journal of Surgical Research, vol. 34, 1983, pp. 205–212.

Marini et al., "Reexamination of the Polymerization of Pyridoxylated Hemoglobin with Glutaraldehyde", Biopolymers, vol. 29, 1990, pp. 871–882.

McGarrity, et al., "Hemoglobin–Based Blood Substitutes: Characterization of Five Pyridoxal 5'-Phosphate Derivatives of Hemoglobin", Journal of Chromatography, vol. 419, 1987, pp. 37–50.

Van Der Plas, et al., "Preparation and physical characteristics of a hemoglobin solution modified by coupling to 2–nor–2–formylpyridoxal 5'–phosphate", Transfusion, vol. 27, 1987, pp. 425–430.

*Primary Examiner*—Howard E. Schain
*Attorney, Agent, or Firm*—Michaelson & Wallace; Peter L. Michaelson; Edward M. Fink

[57] ABSTRACT

The described invention relates to an essentially stroma-free hemoglobin composition evidencing properties suitable for use as a universally applicable blood plasma expander and to a method for the preparation thereof. Typical, of these properties are desirable oxygen affinity values, desirable vascular retention time and substantial absence of toxic side effects. The described composition comprises human hemoglobin cross-linked intramolecularly through the beta-chains and polymerized with glutaraldehyde. Intramolecular cross-linking is typically effected with 2-nor-2-formylpyridoxal 5-phosphate or a bis-pyridoxal polyphosphate.

15 Claims, 3 Drawing Sheets

FIG. 1a  Hb/HbNFPLP AFTER COUPLING

FIG. 1b  HbNFPLP AFTER PURIFICATION ON DEAE-SEPHACEL

FIG. 2  FPLC ANALYSIS POLYHbNFPLP WITH GEL FILTRATION

HEMOGLOBIN COMPOSITION AND PREPARATION THEREOF

RELATED APPLICATIONS

This application is a Continuation-in-Part application of Ser. No. 08/281,260, filed Jul. 27, 1994, now abandoned, which was a continuation of application Ser. No. 07/777,353, filed Feb. 10, 1992, now abandoned.

BACKGROUND OF THE INVENTION

Hemoglobin solutions have potential application in injured man as oxygen-carrying plasma expanders in those situations in which the filling of the vascular system and the oxygen-transporting capacity of the blood are insufficient. The advantage over erythrocytes or blood is that the solutions are universally applicable without typing blood groups. A further advantage is that the hemoglobin solutions have a longer storage life. For this purpose, however, it is necessary to prepare and modify hemoglobin from erythrocytes in such a manner that the three main problems of hemoglobin solutions are minimized. These three problems are:

1) the presence of residues of membrane fragments (stroma) originating from erythrocytes,
2) the high intrinsic oxygen affinity outside the environment of the erythrocyte, and
3) the short retention time in the circulation because (dissociated) hemoglobin disappears rapidly from the vascular system because of leakage through the kidneys.

As early as 1967, Rabiner described a technique for the preparation of hemoglobin solutions in which stroma was removed by filtration and centrifugation so that earlier observed coagulation problems encountered in the kidneys of dogs could be avoided (J. Expl. Med. 126, 1127–1142 (1967). This method for the removal of stroma was subsequently found to be inadequate to obviate many of the side effect encountered.

In 1972 Benesch et al, (Biochemistry 11, 3576–3582 (1972)) determined that a marked decrease of oxygen affinity could be realized by covalently binding pyridoxal 5-phosphate (PLP) to hemoglobin. This permanent bonding was found to prevent PLP from leaving the free hemoglobin infused into the circulation, as would be the case with 2,3-di-phosphoglycerate (2,3-DPG). PLP can also be bound at different sites to one of the β-globin chains in the 2,3-DPG binding cavity.

By polymerizing hemoglobin, the retention time in the circulation can be prolonged. This is described by Mazur et al (U.S. Pat. No. 3,925,344 (1975)) with (m) ethyl glutarimidate, (m) ethyl succinimidate and (m) ethyl suberimidate, etc. and by Bonsen et al (U.S. Pat. Nos. 4,001,200, 4,001,401, 4,053,590 and 4,061,736 (1977)), inter alia with different dialdehydes, particularly glutaraldehyde- A problem encountered with these modifications of hemoglobin is that the oxygen affinity substantially increases so that the oxygen release in vivo to the tissues cannot be optimal. By both coupling hemoglobin to PLP and polymerizing hemoglobin with glutaraldehyde Bonhard et al (U.S. Pat. Nos. 4,136,093 and 4,336,248 (1979)) have obtained a slight improvement in the oxygen affinity in combination with a prolonged retention time. Rausch et al (WO 88/03408) describe polymerization of bovine hemoglobin in which a long circulation time in test animals has been shown. The difference in species, however, will stand in the way of administration to human beings.

Notwithstanding these improvements, clinical application had not yet been relied upon since the administration of small amounts of hemoglobin solution to healthy volunteers showed toxic effects (Savitsky et al, Clin. Pharmacol. Ther. 23, 73–90 (1978)). More recently, however, a group led by Moss administered a comparable dose to healthy volunteers with no side effects being observed. The hemoglobin solution then used was a polymerization product of HbPLP analogous to that produced according to Bonhard but improved as described in WO 87/07832 (Sehgal et al). According to this patent, unconverted hemoglobin must be removed from the polymerization mixture (to prevent negative effects on the renal function), which is achieved by ultrafiltration, gel filtration, and affinity chromatography.

Still another approach to prolonging the retention time in the circulation and decreasing the oxygen affinity is intramolecular cross-linking. Thus, dissociation of tetrameric Hb into dimers and leakage through the kidneys are prevented. Cross-linking of the β-chains was first shown to prolong the retention time by Bunn et al with the use of bis(N-maleidomethyl)ether (J. Exp. Med. 129, 909–934 (1969)). This modification, however, led to a considerable increase in the oxygen affinity. Bakker et al (Adv. Exp. Med. Biol. 180, 345–356 (1985)) showed that by coupling with 2-nor-2-formylpyridoxal 5-phosphate (NFPLP; see formula 1 of the sheet of formulae), as described by Benesch et al (Biochem. Biophys. Res. Commun. 63, 1123–1129 (1975)), both a longer retention time and a lower oxygen affinity are realized. Walder et al use diaspirin compounds for coupling α-globin chains (US patents 4,598,604 and 4,600,531 (1986)). The oxygen affinity of their coupling product is equal to that of erythrocytes and the retention time in the circulation is prolonged by a factor of 3. Bucci et al (U.S. Pat. No. 4,584,130 (1986)) couple hemoglobin intramolecularly to negatively charged organic reagents. Kavanaugh et al use the bifunctional reagent 4,4'-diisothiocyanostibene-2,2'-disulfonate (Biochemistry 27, 1804–1808 (1988)). Their coupling product has a physiologic oxygen affinity but is obtained in low yield.

The modification closest to the physiologic situation is the coupling with NFPLP or later mentioned analogous compounds. This led to coupling of the β-chains through valine-1 of the first β-chain and lysine-87 of the second β-chain (Arnone et al, J. Mol. Biol. 115, 627–642 (1977)). The NFPLP is covalently bound and is permanently present at the site where 2,3-DPG in the erythrocytes influences the oxygen affinity. This β-chain coupling was first described by Benesch et al in 1975 and elaborated further by Van der Plas et al (J. Lab. Clin. Med. 108, 253–360 (1986, Transfusion 27, 425–430 (1987), Transfusion. 28, 525–530 (1988)). They found a substantially decreased oxygen affinity, which guarantees a proper oxygen release under the most frequent conditions. The retention time in the circulation is prolonged by a factor of 3 (Bleeker et al, J. Lab. Clin. Med. 108, 448–455 (1986)). As a plasma expander with oxygen-transporting capacity, however, the cross-linked hemoglobin (HbNFPLP) is open to criticism for the following reasons:

1) the half-life period in the circulation of man will be about 8 hours, whereas 24 hours is desirable, and
2) the oxygen-transporting capacity cannot be more than half of that of normal blood, because the free hemoglobin can only be present in a concentration of maximally 6–7 g/100 ml in the circulation in view of the colloid-osmotic pressure.

BRIEF DESCRIPTION OF THE INVENTION

In accordance with the present invention it has now been found that these prior art problems may be effectively obviated by polymerizing the HbNFPLP. The invention takes advantage of several of the earlier mentioned improvements. Instead of NFPLP, bis-pyridoxal polyphosphate compounds of formula 2 of the sheet of formulae, as recently described by Benesch and Kwong (Biochem. Biophys. Res. Commun. 156, 9–14 (1988)) have proved useful as a starting material for the polymerization product described. The modified hemoglobin according to the invention is briefly indicated by poly HbX1β, "Hb" indicating hemoglobin, "X1β" an intramolecular cross-linking through the β-chains (e.g., by means of -NFPLP or by means of bis-pyridoxal polyphosphates), and "poly" indicating that the intramolecularly cross-linked hemoglobin is polymerized. The invention described herein represents the first time that hemoglobin has been subjected both to an intramolecular cross-linking and a polymerization. Heretofore, workers in the art had only employed one cross-linking treatment which was either an intermolecular cross-linking, that is, polymerization, or an intramolecular cross-linking.

In contrast thereto, the present invention does not simply combine a polymerization with any intramolecular cross-linking but specifically with an intramolecular cross-linking through the beta chains. This unique processing combination has been found to yield new and unexpected results. The hemoglobin so produced which is both intramolecularly cross-linked through the beta chains and polymerized evidences a remarkably low oxygen affinity with a long retention time in circulation and is produced in an unusually safe process which does not require an expensive purification process to remove non-polymerized hemoglobin. This is of particular interest since heretofore an elaborate three step ultrapurification process was required. In the instant case, this purification procedure is not required because the starting product for the polymerization is an intramolecularly cross-linked hemoglobin which essentially prevents the presence of dissociable (dimeric) hemoglobin in the end product. It was surprisingly determined that the product produced in accordance with the invention requires only one purification step and yields an intermediate β-cross-linked hemoglobin in a yield of the order of 79%, said intermediate being capable of being converted by polymerization to an end product containing less than 0.9% hemoglobin. Additionally, the intramolecularly cross-linked hemoglobin is heat stable and remains in solution during heat treatment. As a result, the hemoglobin of the invention can be obtained by a far more economical process than that of the prior art in a far greater yield. Still another important characteristic of the intramolecularly cross-linked and polymerized product of this invention is the unexpected superior stability during storage. The pyridoxilated and polymerized end product described by the prior art workers carries a risk of the formation of toxic hemoglobin αβ-dimers during storage.

DETAILED DESCRIPTION OF THE INVENTION

The product of this invention is a blood substitute comprising a human hemoglobin intramolecularly cross-linked through two β-chains and polymerized. Human hemoglobin is a tetramer built up of two identical α-polypeptide chains and two identical β-chains which are non-covalently bound to each other. The tetramer can dissociate rapidly into two α,β-dimers. Dissociation into α,α- and β,β-dimers or into α- and β-monomers does not take place under physiologic conditions. To prevent that dissociation into α,β-dimers and thus leakage through the kidneys, the hemoglobin is first modified in such a manner that it comprises a covalent, intramolecular cross-link between the β-chains. The modification is effected by means of a reaction of deoxygenated hemoglobin with a water-soluble bifunctional reagent, as the earlier mentioned NFPLP or one of the bis-pyridoxal polyphosphate compounds. After having purified the thus modified hemoglobin with an ion exchange column, it not only shows an increased retention time in the circulation but also a substantially decreased oxygen affinity. By subsequently polymerizing the modified hemoglobin the oxygen affinity is corrected again to an almost physiologic value. Moreover, the retention time in the circulation of the cross-linked polymerized hemoglobin (polyHbX1β) substantially increased. The polymerization is effected with a polymerizing reagent, preferably glutaraldehyde. During this process the molecular weight distribution is analyzed by means of gel permeation chromatography. The successive steps in the process of production will now be discussed in more detail.

The starting material for the preparation of the product of the invention herein described is fresh human blood screened for hepatitis B and HIV. Erythrocytes are isolated therefrom by removing the plasma by centrifugation, the leucocytes by adsorption to a leucocyte filter (Cellselect, NPBI), and the thrombocytes by removing the "buffycoat", after which the erythrocytes are washed three times with 0.9% NaCl. The purified sterile erythrocytes are the starting material for the process proper which is carried out as a whole between 2° C. and 10° C., with the exception of the coupling which is effected at room temperature. At the end of each individual step of the process of production the modified or unmodified hemoglobin is always sterilized by filtration over a sterile 0.2 μm filter (Millipore).

The erythrocytes can be lysed by adding at least two volumes of distilled water. For separating the hemoglobin and the remainders of the red cells (Stroma) cross-flow ultrafiltration is applied in a Pellicon system (Millipore). Preferably, however, the erythrocytes are dialyzed on a similar Pellicon system against a hypotonic phosphate-buffered salt solution, resulting in that the red cells swell to the extent that the hemoglobin can leak to the outside. Since in this procedure the erythrocytes remain substantially intact, the thus obtained hemoglobin solution will contain fewer cell debris (membrane fragments, phospholipids).

The synthesis of the reagents ensuring the specific intramolecular coupling of the hemoglobin is an organochemical procedure which in the case of NFPLP consists of five steps, the starting material being pyridoxal hydrochloride. In the first step the N atom of this molecule is oxidized, and in the second step the oxygen is rearranged to the adjacent methyl group. In the third step the thus obtained alcohol is oxidized in an aldehyde. In the fourth step the two aldehyde groups are coupled with toluidine to the 2-nor-2-formylpyridoxal bistoluidine. This gives protection of the aldehyde groups in the last fifth step of the synthesis, the phosphorylation of the methyl alcohol group of the molecule with polyphosphoric acid. After separation of the toluidine groups by hydrolysis the resulting NFPLP is separated from inorganic phosphate by means of a cation exchange column.

For the synthesis of bipyridoxal polyphosphates, first the tetrabutylammonium salt (TBA) of PLP is reacted with diphenylphophochloridate (DPPC, Aldrich). To the crude reaction product is added the TBA salt of the desired phosphate. The reaction mixture is then separated on an anion exchange column (Dowexl-X8) with a gradient from 0 to 0.2 molar LiCl in a 0.01 molar HCl solution as an eluent.

Figure 1A:
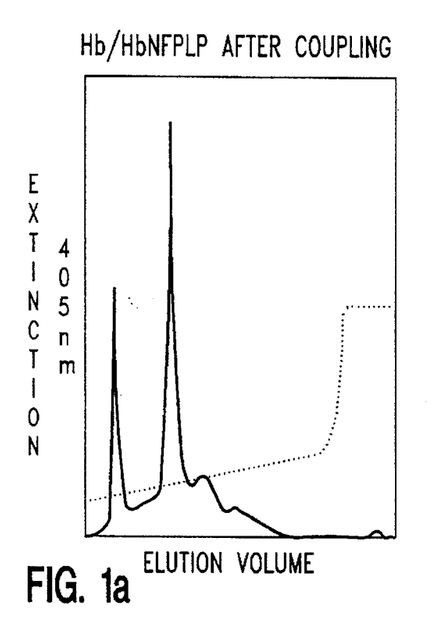

The stroma-free hemoglobin is then coupled to NFPLP or a bispyridoxal polyphosphate compound in a molar ratio varying from 1:1 to 1:2. The coupling reaction takes place in a trishydrochloride buffer having a final concentration of about 0.1 molar and a pH of about 7.0. The hemoglobin solution is first deoxygenated completely, which may be done in a rotating flask into which nitrogen or another inert gas is introduced. Preferably, however, a gas exchanger is used (Endotronics), with the hemoglobin being circulated through flexible tubes that are substantially impermeable to oxygen (Tygon). By adding an excess of a reducing agent, preferably sodium borohydride (Merck), to the coupling mixture, the cross-link becomes irreversible and the binding covalent. A typical example of an analysis of a coupling mixture by means of ion exchange chromatography (Mono Q, Pharmacia) is shown in FIG. 1a. The coupling hemoglobin is dialyzed on the Pellicon system against a trishydrochloride buffer with a concentration of about 0.1 molar and a pH of about 8.3 to remove the excess of reagents and to create the right conditions for the next step in the process, the purification.

Figure 1B:
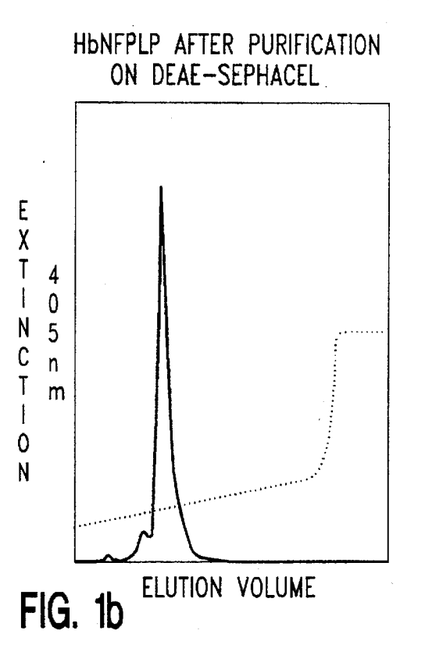

The coupled hemoglobin (HbX1β) is next purified with ion exchange chromatography. On a column filled with anion exchanger of the tertiary amine type, preferably diethylaminoethyl-A50, diethylaminoethyl-Sephacel or diethylaminoethyl-Sepharose (Pharmacia) HbX1β) is separated from uncoupled hemoglobin by means of a linear salt gradient with which the column is eluted. The salt gradient consists of an increasing concentration of sodium chloride from 0 to about 0.1 molar in the above tris-buffer with a pH of 8.3. Detection of hemoglobin is effected spectrophotometrically in a flow cuvette. The purified HbX1β is then collected separately from the other eluate by means of an automatically controlled valve (Pharmacia). A typical example of an analysis of the purified HbX1β is shown in FIG. 1b. This purification step results in a specific product, in which there also occurs a substantial reduction of possibly toxic substances, such as membrane fragments of the erythrocyte, endotoxin, and viral antigens, as far as these are present in the stroma-free hemoglobin.

Subsequently, the purified HbX1β is polymerized with, preferably, glutaraldehyde (Sigma) which is done by means of a kidney dialysis filter (Andante, Organon Tecknika). This filter comprises a large number of "hollow fibers" of a semipermeable membrane through which small molecules, such as water, salts, and also glutaraldehyde, can migrate freely to and fro, which large molecules, such as hemoglobin, cannot. Thus it is rendered possible to control the velocity of the polymerization reaction, because the glutaraldehyde can be added to the hemoglobin gradually and in small portions. The reaction time and the amount of added glutaraldehyde depends on the amount of HbX1 β and the desired molecular weight distribution of the final product. The polymerization results in a mixture of products that can be analyzed by gel permeation chromatography (Superose 12, Pharmacia). By such an analysis method the mixture can be separated into monomers, dimers, trimers, tetramers, and polymers. The ratio of these different polymers in the final product depends on the reaction time and the reaction velocity. Thus the mixture may vary in the following ratios (percentages of the total):

| polymers | tetra/trimers | dimers | monomers |
| --- | --- | --- | --- |
| 0 | 0 | 20 | 80 |
| 0 | 40 | 20 | 40 |
| 20 | 40 | 15 | 25 |
| 40 | 30 | 10 | 20 |

Figure 2:
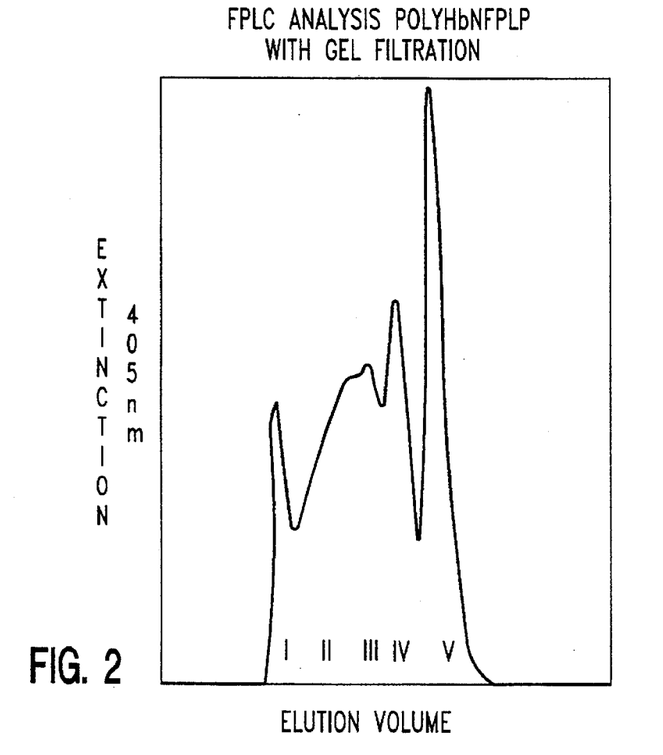
FIG. 2—Polymer composition of polyHbNFPLP, determined by gel filtration over a Superose 12 column. The elution pattern shows the following peaks: I—polymers larger than tetramer II—tetramers, III—trimers, IV—dimers, V—monomers.

Finally, the whole mixture will consist of large polymers, unless the reaction is stopped in time. This may be done by adding an excess of lysine to the reaction mixture so that the free aldehyde groups still present are blocked and the polymerization stops. By adding a reducing reagent, preferably sodium borohydride, the cross-links become covalent. Thus a stable final product can be obtained. When determining the optimum degree of polymerization of the final product (polyHbX1β), consideration must be given to the retention time in the circulation, but also to the effects of the polymerization on the colloid osmotic pressure and viscosity of polyHbX1β. At an equal Hb concentration the colloid osmotic pressure will decrease with an increasing degree of polymerization, but the viscosity will increase. FIG. 2 shows a typical example of a gel filtration pattern of polyHbX1β. Of the final product, preferably 10% consists of polymers, 40% of tetra/trimers, 20% of dimers, and 30% of monomers. Such a degree of polymerization ensures that the retention time of polyHbX1β in the circulation of rats is prolonged by a factor of about 7 when compared with unmodified hemoglobin. The colloid osmotic pressure is then reduced to such an extent that under physiologic conditions a concentration of 10 g/100 ml is possible and the viscosity only slightly increases to a value comparable to that of plasma (see FIGS. 3 and 4). The molecular weight of monomer Hb is 68 kD; the different polymers are multiples thereof. The polymer fraction elutes with the void volume of the column which is used by routine for the gel filtration analyses. Analyses on columns with another range in separating capacity have shown that the molecular weight of the polymer fraction of polyHbX1β ranges from 300 to 600 kD. The average molecular weight of the final product can be derived from the ratio of the different polymers in poly-HbX1β and will approximately range from 160 to 270 kD, particularly from 160 to 220 kD, although the average molecular weight may vary from 140 to 380 kD. Consequently, the average polymer is polyHbX1β has a size ranging between dimer and trimer. The monomer fraction in the final product is 30%, but need not be removed therefrom, since the hemoglobin is coupled intramolecularly and is consequently not nephrotoxic.

ADVANTAGES OF THE INVENTION

The invention herein described has the following advantages over existing products:

1) A first advantage concerns the intermediate product HbX1β. This is obtained by specific coupling of an aldehyde to both β-chains of Hb. HbX1β is formed with a yield of at least 70% and can be separated from unconverted nephrotoxic Hb by a single purification step with an ion exchanger. Coupling of Hb to PLP gives 4–6 products of which only 25% main product.

2) PolyHbX1β is a mixture of polymers which also comprises non-polymerized HbX1β. An important advantage is that this non-polymerized HbX1β need not be removed. In fact, HbX1β cannot dissociate into dimers through the intramolecular cross-link so that it is not filtered through the kidney and does not cause, e.g., nephrotoxicity. This is contrary to, e.g., polyHbPLP the non-polymerized HbPLP of which is nephrotoxic so that it is necessary to remove this carefully by means of complicated purification steps. This fact enables a simpler process of producing polyHbNFPLP and consequently a higher efficiency.

3) The oxygen affinity of polyHbX1β is lower than that of polyHbPLP (Sehgal so that in vivo a better oxygen release must be possible.

4) The preparation is started from human erythrocyte suspensions purified from leucocytes, thrombocytes and plasma proteins by filtration and centrifugation so that contamination with metabolites and other substances from these fractions is avoided.

5) The stroma removal from the hemoglobin solutions is measured by means of the phospholipid content and the membrane antigen glycophorin-α. The phospholipid content is lower than 4 µg/g Hb (erythrocytes: 9 mg/g Hb). The amount of glycophorin-β is less than 0.01% of what is present in erythrocytes.

6) PolyHbX1β can be prepared in the following ratio: 30% monomer, 20% dimer, 40% tri/tetramer and 10% polymer. Then the said solution has an iso-oncotic hemoglobin concentration of 10 g/100 ml and a relative viscosity lower than 2 with respect to water. For polyHbPLP Bonhard described that a hemoglobin content of maximally 8 g/100 ml can be reached, whereas the product of Sehgal already has a viscosity of 3 cp at 8 g/100 ml.

7) The catabolism of HbNFPLP is already properly understood, which is important to the evaluation of possible side effects. No accumulation of HbNFPLP has been found to occur in liver or kidneys (Bleeker et al, J. Lab. Clin. Med. 113, 151–171 (1989)). It has been shown that the coupling molecule, NFPLP, is substantially excreted in urine and feces within 8 days.

8) A number of measures and steps taken in the process of production result in that contamination with viruses, if any, is almost impossible: inter alia, by screening donors, using leucocyte filtration and ion exchange chromatography of the coupling mixture.

EXAMPLES

The practice of the present invention will be explained by reference to the following detailed examples It will be understood that these examples are set forth solely for illustrative purposes, are not to be construed as limiting and elucidate the reproducibility of the invention, but in no way mean the definitive conditions of the different steps of the process of production and comprise the complete scope of the invention. All operations were carried out under sterile conditions (GMP standards) and all the steps of production were effected at about 5° C. and under atmospheric pressure, with the exception of the coupling reaction which was carried out at room temperature.

Example 1

PolyHbNFPLP

A. Preparation of a stroma-free hemoglobin solution.

Fresh human blood was released from plasma by centrifugation, from leucocytes through a leucocyte filter and from thrombocytes by removal of the buffy-coat. The units of red blood cells were washed three times in sterile plastic bags with 0.5 10.9% NaCl and centrifuged for 5 minutes at 3200 rpm. The washed erythrocytes ("packed cells") of 8 units were pooled and suspended in 4 volumes of a 0.1 molar NaCl solution buffered with 0.01 molar phosphate, which results in a 6–8 l suspension with a hematocrite of 20–30%. On the Pellicon system provided with a 0.45 µm cut-off HVLP cassette (Millipore) this suspension was dialyzed first against about 5 l of the phosphate buffered 0.1 molar NaCl solution and then against a phosphate buffered 0.05 molar NaCl solution. When the hemoglobin began to leak from the cells. the filtrate was collected. Usually about 15 to 20 l of filtrate is collected and then concentrated on the same Pellicon system but now provided with a 10,000 dalton cut-off PTGC cassette. The ultrafiltrate has a hemoglobin concentration of 10 to 20 g/100 ml and was sterilized by filtration. The yield of stroma-free hemoglobin solution was 80–90%, and the methemoglobin content was below 1%. The phospholipid content in the hemoglobin solution was below 4µg/g Hb.

B. Synthesis of NFPLP

This is a 5-step synthesis starting from pyridoxal hydrochloride (Merck).

1. The synthesis of the N oxide.

a. 200 g of pyridoxal hydrochloride was dissolved in 2 l of ethanol (96%) and boiled. After 1 hour of refluxing the solution was cooled, and an equivalent of sodium bicarbonate (84 g) added cautiously. The solution was refluxed for 30 minutes. The salt precipitate was filtered over "Celite Hyflo-Super-Cel" (hyflo, Merck) and rinsed with a small amount of ethanol (96%). The thanolic solution was further used for reaction b.

b. The solution of the pyridoxal ethyl acetal was cooled to $-30°$ C. with $CO_2$/acetone. For half an hour a solution of 345 g of methachloroperbenzoic acid (Aldrich) in 1 l of ethanol ($-10°$ C.) was added with stirring. The light-yellow reaction mixture was allowed to stand for 40 hours at $-30°$ C. The N oxide crystallized out into white crystals, was filtered and washed with ether.

2. The rearrangement of the N oxide.

a. 35 g of N oxide and 100 g of trifluoroacetic anhydride (Aldrdich) were cooled to $-30°$ C. The trifluoroacetic acid was dropped slowly to the solid N oxide, and the suspension stirred for 12–24 hours at room temperature. Then the dark red solution was hydrolyzed with 40 ml 2 molar HCl and refluxed for 1 hour.

b. After evaporation, the residue was dissolved in a minimum amount of methanol, and tetrahydrofuran (THF) added until the solution becomes turbid. Crystallization occurred overnight at $-30°$ C.

3. The oxidation with pyrolusite.

In a mixture of 50 ml of methanol and 200 ml of THF, 6 g of the HCl salt was dissolved, 25 g of activated manganese dioxide (Merck) added, and the mixture stirred for 12–24 hours at room temperature. The reaction was followed by thin-layer chromatography (TLC, Merck) with an eluent of chloroform/methanol (95/5). The pyrolusite and the resulting manganese chloride were filtered over hyflo and washed with methanol. Silica gel was added to the filtrate and then evaporated. The silica gel was eluted with successively 800 ml of chloroform and 500 ml of chloroform/methanol 97.5/2.5. The solution was then evaporated.

4. The preparation of 2-nor-2-formylpyridoxal bistoluidine.

In boiling water, 4 g of 2-nor-2-formylpyridoxal was hydrolyzed to the free dialdehyde. The reaction was followed by TLC. The solution was poured slowly into a solution of 6.6 g of p-toluidine (Merck) in 100 ml of methanol and refluxed until turbidity of the solution was observed. After cooling to room temperature the solution was allowed to stand overnight at 4° C. The orange precipitate formed was filtered and washed with cold dry ether.

5. Phosphorylation.

Polyphosphoric acid (PPA) was made from a mixture of 10 g of $P_2O_5$ and 13 g of $H_3PO_4$. 15 ml of PPA was added to 1.5 g of bistoluidine. The reaction mixture was stirred for 1 hour at 60° C, shut off from the air. Then 7.5 ml of 0.1N HCl is added. This reaction mixture was stirred for 15 minutes at 60° C. The dark purple mixture was applied to a column, filled with a cation exchanger (Biorad 50W×80; H form, 200–300 mesh) and eluted with distilled water. The eluate was collected in 10 ml fractions.

With the Molybdate test (W.C. Hulsman, thesis of 1958, Amsterdam) there was measured which fractions contain free phosphoric acid. The fractions containing organic phosphate ($A_{415}$ in 1M phosphate buffer (pH=7) in 1:100 dilution >0.1 absorption unit) were pooled. The NFPLP is stored as a pool at 4° C. in the dark.

Coupling of NFPLP to the stroma-free hemoglobin

The stroma-free hemoglobin solution was dialyzed on the Pellicon system against 10 volumes of 0.1 molar tris-hydrochloride solution with a pH of 7.0. Usually about 1 l of 10 g/100 ml hemoglobin was coupled, but the volume can be easily scaled up. The hemoglobin solution having a pH varying from 6.9 to 7.1 is deoxygenated by means of a membrane gas exchanger through which nitrogen gas was passed at a rate of 2 l/min. The hemoglobin solution was pumped through the gas exchanger from a closed reservoir at a rate of 0.5 l/min. (Sarns pump). Within 1 hour the oxygen was removed, which was monitored by means of an oxygen saturation measurement (below 5%, measured by multicomponent analysis on a diode array spectrophotometer (Hewlet-Packard)). If desired, the hemoglobin can also be deoxygenated in a closed rotating flask having a volume of 10 l into which nitrogen is introduced. This procedure gives the same result as regards the content of deoxyHb, but takes three to five times longer.

To the deoxygenated hemoglobin solution in the reservoir a deoxygenated aqueous solution of NFPLP was added slowly. The molar ratio relative to hemoglobin may vary from 1:1 to 2:1. Mostly, a small excess of NFPLP was added. The reaction time is at least 1 hour. Then a 20-fold excess of sodium borohydride was added to the coupling mixture. The sodium borohydride was dissolved in 30–50 ml of a 0,001 molar KOH solution which is also deoxygenated. Since nitrogen can also be introduced into the reservoir, the gas formation occurring during reduction causes no problem and is therefore discharged together with the nitrogen. At the end of the reaction the excess of reagents was removed by dialysis and the coupling mixture sterilized by filtration. The maximum yield of coupled hemoglobin is 60–70%, which can be determined with the integrating of the peaks of a chromatogram obtained in an FPLC analysis of the mixture on an ion exchange column (see FIG. 1a). With increasing salt concentration first Hb and then HbNFPLP was eluted from the column.

D. Purification of HbNFPLP

At the end of the reaction the coupling mixture was dialyzed against 10 volumes of the starting buffer of the ion exchange chromatography, a 0.1 molar tris-hydrochloride buffer having a pH of 8.3. A column of 25 to 5 cm was filled with diethylaminoethyl Sephacel in starting buffer and eluted with at least 5 column volumes of that starting buffer at a rate of 2 ml/min. (Cenco pump). Subsequently, 200 ml of the coupling mixture of maximally 10 g/100 ml was applied to the column and then eluted with at least 1 column volume of starting buffer. The column is then eluted with a gradient of 0–0.1 molar NaCl in about 3 l of starting buffer. Analysis of the different fractions takes place spectrophotometrically by means of a flow cuvette at 540 nm. The different fractions (uncoupled Hb and HbNFPLP) can be collected by means of an automatically controlled valve apart from the other eluate. The purified HbNFPLP was concentrated on the Pellicon system (PTGC cassette) and sterilized by filtration. Analysis of the purified product took place by FPLC ion exchange chromatography (see FIG. 1b). More than 95% of the thus obtained HbNFPLP was pure. After this column purification the yield of HbNFPLP is 40–50% of the coupling mixture, which corresponds to 70–80% of the coupled product.

E. Polymerization of HbNFPLP

The purified HbNFPLP was polymerized by means of a kidney dialysis filter. The HbNFPLP solution was pumped through the artificial kidney from a reservoir at a rate of 0.3 l/min., while a dialysate phosphate buffered NaCl solution (PBS) was circulated at a rate of 0.5 l/min (Sarns pumps). To the dialysate 1 ml of 25% glutaraldehyde is always added stepwise, and the velocity of the polymerization reaction is monitored by means of gel filtration analyses. The amount of glutaraldehyde required to obtain a certain degree of polymerization depends on the amount and concentration of the employed HbNFPLP solution. A typical example of a gel filtration analysis of a final product is shown in FIG. 2. In this case the final product consists of 10% polymer, 40% tetra/trimer, 20% dimer, and 30% monomer, which is the desired ratio, but in principle the degree of polymerization depends on the reaction time. Starting from 0.5 l of 5 g/100 ml HbNFPLP at least 5 ml of 25% glutaraldehyde is required to reach such a final stage as shown in FIG. 2 within a reasonable time (a few hours). Per 1 mole of hemoglobin at least 8 moles of glutaraldehyde are added. The reaction can be stopped by adding to the reservoir a 10-fold excess, relative to glutaraldehyde, of 1 molar lysine solution with a pH of about 7.0. Also, the dialysate is pumped out and replaced by new PBS. The dialysis is continued for some hours, and by replacing the dialysate a number of times the polyHbNFPLP can be introduced into any desired buffer, for exchange transfusions preferably in kidney dialysis buffer. Sometimes the thus produced polyHbNFPLP slowly polymerizes further in the months to flow, which is preferably avoided by also adding to the polymerization mixture, after the polymerization reaction with lysine has stopped, an amount of sodium borohydride equimolar with respect to glutaraldehyde so as to give a stable final product. After dialysis the polyHbNFPLP may be concentrated and sterilized by filtration. The yield of the polymerization reaction is almost 100% and the methemoglobin content in the final product is below 5% (multicomponent analysis). The phospholipid content is determined by extracting phospholipids from the polyHbNFPLP solution by means of chloroform and methanol. The extract is treated with perchloric acid and the released phosphate forms a complex with ammonium molybdate and malachite green (Merck), the absorption of which is measured at 630 nm. The content in the final product is below 1 µg/g Hb, which means a reduction by a factor of 4 relative to the stroma-free hemoglobin solution. The amount of glycophorin-α in the final product is below the detection limit of the determination for this erythrocyte membrane antigen (radioimmunoassay with monoclonal antibody), which reflects a value belower 0.01% of what is present in erythrocytes. The endotoxin content is determined with the Limulus test (Bleeker et al, in Progress in Clinical and Biological Research, vol. 189: Bacterial Endotoxins, 293–302 (1985), eds. ten Cate et al) and is below 2 EU/g Hb for polyHbNFPLP.

F. Biophysical characterization of polyHbNFPLP

Polymerization influences some properties of the hemoglobin solution which are essential in case of use as a blood substitute: the colloid osmotic pressure, the viscosity, and the oxygen affinity.

1. Colloid osmotic pressure

Figure 3A:
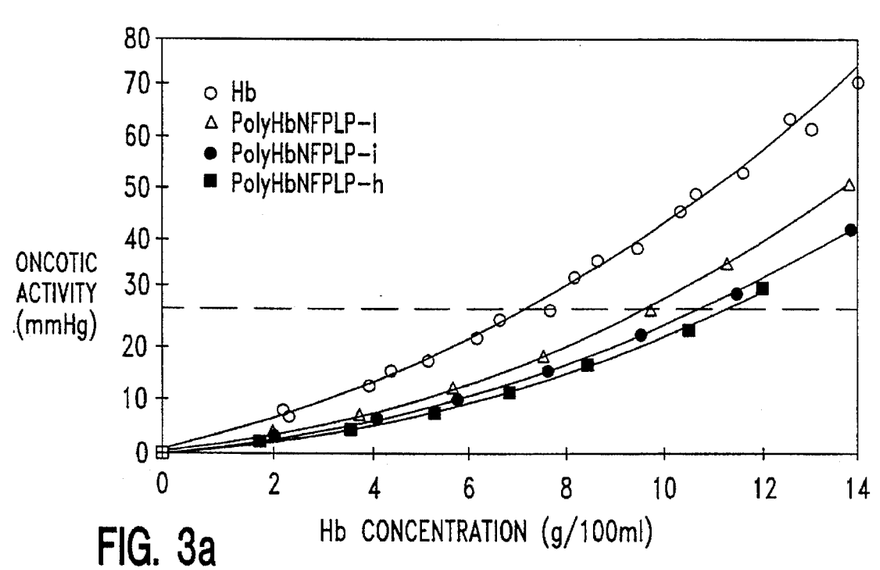

When the polymerization proceeds further, the colloid osmotic pressure which may be caused by the solution decreases. FIG. 3a shows the relation between the concentration and the colloid osmotic pressure for different hemoglobin solutions. The colloid osmotic pressure is determined with a pressure transducer (Statham P23Db) over an ultrafilter membrane. The concentration is determined photometrically. The horizontal dotted line indicates the colloid osmotic pressure of human plasma. Thus it can be seen that the iso-oncotic concentration (i.e. the concentration at which the solution has the same colloid osmotic pressure as plasma) of unmodified hemoglobin (Hb) is 7 g/100 ml. By polymerization the iso-oncotic concentration is increased to about 9 g/100 ml for polyHbNFPLP without large polymers and to about 11 g/100 ml for polyHbNFPLP in which 45% larger polymers are formed. This higher iso-oncotic concentration means that during transfusion a higher plasma concentration can be obtained without the risk of overfilling the vascular system.

2. Viscosity

Figure 3B:
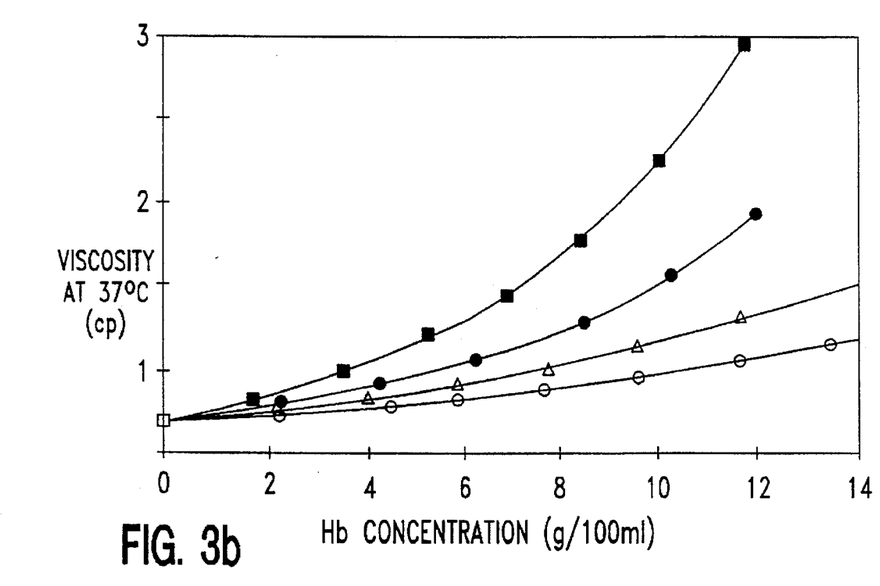

FIG. 3b shows the relation between concentration and viscosity for the same hemoglobin solutions. The relative viscosity is measured with an Ostwald viscosimeter. This graph shows the other side of the polymerization: the increase in the viscosity. At a low degree of polymerization (polyHbNFPLP 0,40,20,40) this increase, however, is still so low that the relative viscosity at 9 g/100 ml is 1.5 and is therefore still below that of plasma. At a higher degree of polymerization (polyHbNFPLP 45,30,10,15) a relative viscosity of 4 has been found at 11 g/100 ml, i.e. a value equal to that for whole blood. This means that the viscosity of polyHbNFPLP remains acceptable if polymerization is not carried out beyond 45% acceptable if polymerization is not carried out beyond 45% polymers (molecular weight ranging from 300 to 600 kD).

3. Oxygen affinity

Figure 4:
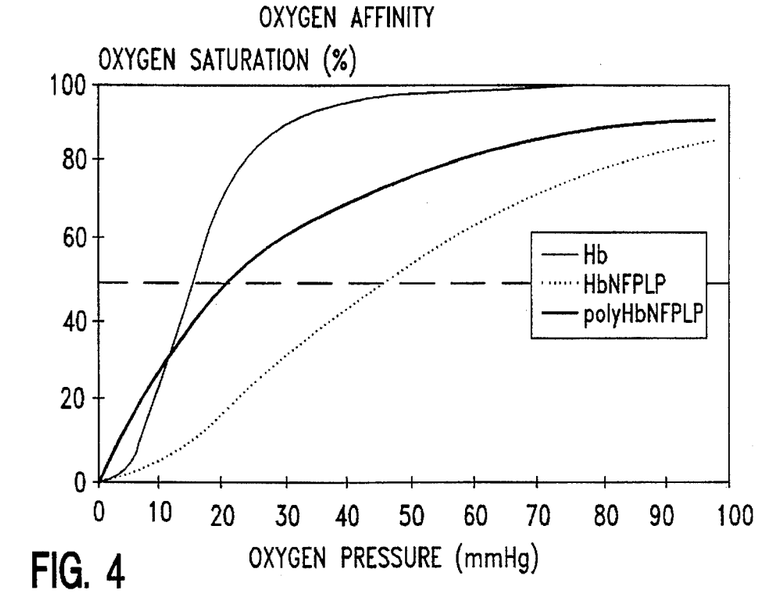
FIG. 4—Oxygen dissociation curves, measured under physiologic conditions of pH, $pCO_2$, and temperature, of an unmodified hemoglobin solution (Hb), HbNFPLP, and polyHbNFPLP.

The oxygen-binding properties have been examined with an oxygen dissociation curve analyzer (DCA, Radiometer), under physiologic conditions of pH, $pCO_2$, and temperature. FIG. 4 shows the measurements of unmodified hemoglobin (Hb), HbNFPLP and polyHbNFPLP. The 50% saturation point, the p50 of polyHbNFPLP is at a $pO_2$ of 22 mm Hg and is thus substantially equal to the p50 of whole blood (26 mm Hg). A clear improvement over the unmodified hemoglobin solution (p50:14 mm Hg) and HbNFPLP (p50:45 nun Hg) has taken place.

G. In vivo characteristics of polyHbNFPLP

1. Retention time in circulation

Figure 5:
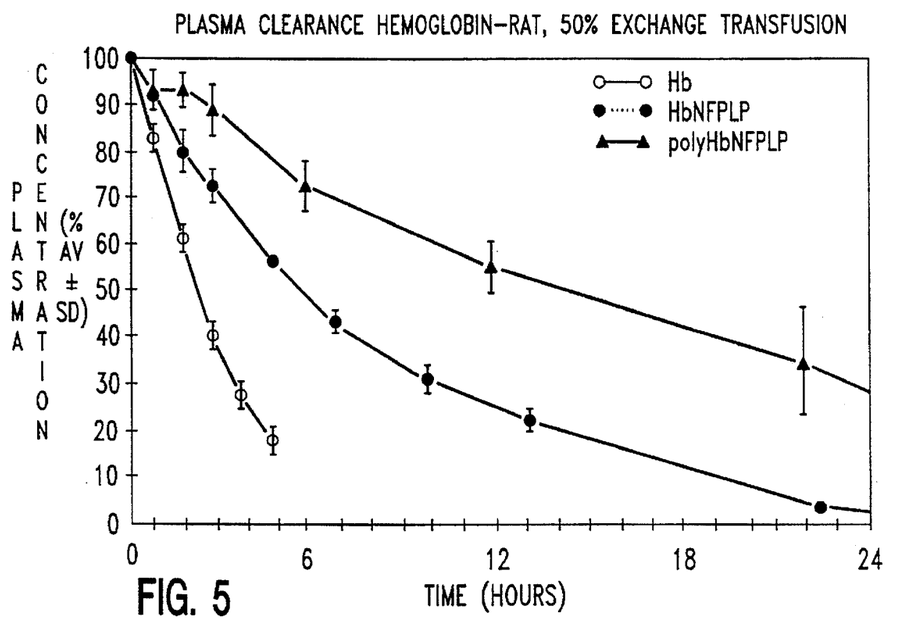
FIG. 5—Plasma disappearance curves of free hemoglobin in rats after replacement of 50% of the blood volume by: 1 - unmodified hemoglobin (Hb, n=5), 2 —HbNFPLP (n=3), and 3-polyHbNFPLP (n=3).

The retention time in the circulation has been examined in rats after replacement of 50% of the blood by a hemoglobin solution. FIG. 5 shows the plasma disappearance curve of polyHbNFPLP with 30–40% polymers, as compared with that of an unmodified hemoglobin solution (Hb) and a hemoglobin solution modified by only intramolecular cross-linking with NFPLP. The moment the plasma concentration is halved (T50%) is at about 2 hours for Hb. Intramolecular cross-linking improves the T50% by a factor of 3. After polymerization the T50% has increased by a factor of 7 with respect to Hb. In view of literature data on research with different hemoglobin solutions in different test animals including apes, a retention time of more than 24 hours is expected for polyHbNFPLP in human beings.

2. Toxicity to the kidney

After replacement of 50% of the blood volume by a hemoglobin solution in rats 40% of the administered dose is excreted in the urine. Histochemical research shows a strong accumulation of hemoglobin in the kidneys, a clear indication of a limited renal function. After intramolecular cross-linking of the β-chains less than 5% of the dose is excreted in the urine, histochemical research only showing a minimum accumulation of HbNFPLP. The occurrence of an impairment of the kidney function caused by HbX1β is therefore improbable. After an exchange transfusion with plyHbNFPLP hemoglobin is not detectable in the urine, nor in the kidneys themselves. Thus an impairment of the kidney function caused by intrarenal precipitates of polyHbNFPLP is therefore impossible.

Example 2 polyHb(bisPL)$P_2$

The preparation of polyHb (bisPL)$P_2$ proceeds identically with that of polyHbNFPLP, as described in Example 1, with the exception of the synthesis of the coupling molecule. The characteristics of the final product (polyHb(bisPL) $P_2$) were also substantially identical with that of polyHbNFPLP. The synthesis of (bisPL) $P_2$ proceeds as follows:

After reaction of 0.002 moles of PLP with 0.0025 mole of DPPC, 0.004 mole of PLP-TBA in 10 ml of dry pyridine was added thereto. After the reaction mixture has been allowed to stand for 1 night, it was applied to an ion exchange column and eluted with 0.01 molar HCl. (BisPL)$P_2$ comes from the column as first fraction, followed by PLP. After neutralization the fraction was evaporated; yield 350 mg product (30%). UV spectrum: maxima at 294 and 335 mn in 0.1 molar HCl, 330(s) and 391 nm in phosphate buffer with a pH of 7, 308 and 391 nm in 0.1 molar NaOH.

DESCRIPTION OF THE FIGURES

FIG. 1—Chromatograms obtained with an anion exchange colunm (Mono Q). Left-hand chromatogram (FIG. 1a): mixture of Hb (left-hand peak) and HbNFPLP (right-hand peak) obtained after the coupling reaction of Hb with NFPLP. Right-hand chromatogram (FIG. 1b): purified main product (HbNFPLP) from the coupling mixture.

FIG. 3—Upper graph (FIG. 3a): relation between concentration and colloid osmotic pressure of an unmodified hemoglobin solution (Hb) and three differently polymerized solutions of polyHbNFPLP. Of the polyHbNFPLP solutions the polymer composition is indicated in percentages (po: polymers, t/t: tetra/trimers. di: dimers, mo: monomers). The horizontal dotted line indicates the colloid osmotic pressure of human plasma.

Lower graph (FIG. 3B): relation between concentration and viscosity of the same hemoglobin solutions.

We claim:

1. A stroma-free hemoglobin composition comprising a polymerized human hemoglobin intramolecularly cross-linked through the two β-chains of the hemoglobin by reaction of a pyridoxal 5-phosphate derivative having two aldehyde groups with one amino group in each β-chain.

2. A hemoglobin composition according to claim 1, in which the hemoglobin is cross-linked intramolecularly through the β-chains by 2-nor-2-formylpyridoxal 5-phosphate of the general formula 3. A hemoglobin composition according to claim 1, in which the hemoglobin is cross-linked intramolecularly through the β-chains by a bis-pyridoxal polyphosphate of the general formula in which R is an oxygen atom, an orthophosphate group, a pyrophosphate group, a diphosphate residue, or a diphosphonate residue.

4. A hemoglobin composition according to claim 1, in which the hemoglobin is polymerized by glutaraldehyde.

5. A hemoglobin composition according to claim 1, in which up to 40% of the hemoglobin is present as monomer unpolymerized hemoglobin.

6. A hemoglobin composition according to claim 1, having an oxygen affinity satisfying a p50 value of 19–24 mm Hg.

7. A hemoglobin composition according to claim 1 in the form of a freeze dried composition.

8. Hemoglobin composition of claim 1 wherein the hemoglobin is polymerized to an average molecular weight within the range of 140 to 380 kD.

9. Hemoglobin composition of claim 1 wherein the hemoglobin comprises a polymerized mixture of from 40 to 50%, by weight, of di-, tri-, and tetramers.

10. Hemoglobin composition of claim 1 having an iso-oncotic hemoglobin concentration of greater than 9 g/100 ml and a relative viscosity less than 4 centipoise.

11. Method for the preparation of a hemoglobin composition which comprises the steps of
 (a) reacting an essentially stroma-free human hemoglobin with a pyridoxal 5' phosphate derivative having 2 aldehyde groups to cross-link the hemoglobin intramolecularly through the two β-chains of the hemoglobin,
 (b) removing any hemoglobin which has not been intramolecularly cross-linked, and
 (c) polymerizing the intramolecularly cross-lined hemoglobin to yield an essentially stroma-free polymerized human hemoglobin which is intramolecularly cross-linked through the β-chains.

12. Method in accordance with claim 11 wherein the stroma-free hemoglobin is coupled to the phosphate derivative in a molar ratio ranging from 1:1 to 1:2 in a trishydrochloride buffer having a final concentration of about 1.0 molar and a pH of about 7.0.

13. Method in accordance with claim 12 wherein the coupled hemoglobin is purified and, subsequently polymerized with glutaraldehyde.

14. Method in accordance with claim 13 wherein purification is effected by ion exchange chromotography and polymerization effected by means of a kidney dialysis filter.

15. Method in accordance with claim 14 wherein polymerization is terminated by adding an excess of lysine to the reaction mixture.

* * * * *